United States Patent [19]

Rosen

[11] Patent Number: 5,104,641
[45] Date of Patent: Apr. 14, 1992

[54] NITROXIDE NMR CONTRAST ENHANCING AGENTS AND THEIR USE IN NMR IMAGING

[75] Inventor: Gerald M. Rosen, Lutherville, Md.
[73] Assignee: M.R.I., Inc., Lutherville, Md.
[21] Appl. No.: 485,068
[22] Filed: Feb. 26, 1990

Related U.S. Application Data

[63] Continuation-in-part of Ser. No. 121,823, Nov. 6, 1987, abandoned, and a continuation-in-part of Ser. No. 836,867, Mar. 7, 1986, Pat. No. 4,834,964.

[51] Int. Cl.$^5$ ............... G01N 31/00; G01N 24/00; A61K 31/40; C07D 207/46
[52] U.S. Cl. .......................... 424/9; 436/173; 514/424; 548/542
[58] Field of Search .............. 424/9; 128/653 A F, 128/653 C A, 654; 436/173; 514/424; 548/542

[56] References Cited

U.S. PATENT DOCUMENTS 3,502,692  3/1970  Feldman et al. ............... 548/531
4,656,026  4/1987  Coffman et al. ............... 424/9

OTHER PUBLICATIONS

Stier et al., "Radical Production in Amine Oxidation by Liver Microsomes", Xenobiotica, vol. 1, Nos. 4/5, pp. 499-500 (1971).
Rauckman et al., "Enzymatic Reactions of Spin Labels", Spin Labeling in Pharmacology, Ed. J. L. Holtzman, Academic Press, pp. 175-190 (1984).
Rosen et al., "Detection of Phagocyte-Derived Free Radicals with Spin Trapping Techniques: Effect of Temperature and Cellular Metabolism", Biochim. Biophys. Acta 969 (1988), pp. 236-241.
Kruch, T. R., "Spin Labeling-Theory and Applications", L. J. Berlinger ed., Academic Press, NY, pp. 339-372 (1976).
Rosen, Gerald M., J. Med. Chem., 17, 358 (1974).
Rauckman et al., J. Med. Chem. 19, 1254 (1976).
Griffeth et al., Investigative Radiology, 19, 1533 (1984).
Rosen et al., Biochem. Pharm. 26, 675 (1977).
Keana et al., Magnetic Resonance in Medicine, 5, 525, 1987.
Brasch, R., "Contrast Agents in Magnetic Resonance Imaging", Exerpta Medica, Pub. 1986, pp. 11-13.
Rosen et al., "Formation and Reduction of a Nitroxide Radical by Liver Microsome" Biochemical Pharmacology, vol. 26, pp. 675-678, Pergamon Press, 1977.
Rosen et al., "Intrathecal Administration of Nitroxides as Potential Contrast Agents for MR Imaging", Radiology, 1987; 163:239-245.
Rauckman et al., "Pharmacological Activity of Nitroxide Analogues of Dichloroisoproterenol and Propanolol", Journal of Medicinal Chemistry, vol. 19, No. 10, pp. 1254-1256, 1976.
Rosen, Gerald M., "Use of Sodium Cyanoborohydride in the Preparation of Biologically Active Nitroxides", Journal of Medicinal Chemistry vol. 17, No. 3, pp. 358-360, 1974.
Maksimova et al., "Synthesis of Spin-Labeled Peptides", Bulletin of the Academy of Sciences of the USSR, Division of Chemical Science, vol. 24, No. 4, Apr. 1975.
Medicinal Chemistry, Second Ed., "6, Relation of Chemical Structure and Biological Activity", p. 43, Burger, ed., Interscience Pub., 1960.
Morrison et al., "Amines II, Reactions", Organic Chemistry, Third Ed. Chap. 23, Sec. 23.5, pp. 752-755, Allyn and Bacon, Inc., 1973.
Keana et al., "Nitroxides as Potential Contrast Enhancing Agents for MRI Application: Influence of Structure on the Rate of Reduction by Rat Hepatocytes, Whole Liver Homogenate, Subcellar Fractions and Ascorbate", Magnetic Resonance in Medicine, 5, 525-536 (1987).
Krugh, Thomas R., "Spin-Label Induced Nuclear Magnetic Resonance Relaxation Studies of Enzymes", in Spin Labeling-Theory and Applications, L. J. Berliner, ed., Academic Press (1976), pp. 339-340.
Grodd et al., "Comparison of Ionic and Non-ionic Contrast Media for Renal Enhancement in NMR Imaging", abstract from 1985 meeting of the Association of University Radiologists.
Keana, John F., "Newer Aspects of the Synthesis of Chemistry of Nitroxide Spin Labels", Chemical Reviews, 1978, vol. 78, No. 1, pp. 37-64.
Couet et al., "Pharmacokinetics and Metabolic Fate of Two Nitroxides Potentially Useful as Contrast Agents for Magnetic Resonance Imaging" Pharmaceutical Research, 1984, pp. 203-209.
Griffeth et al., "Pharmacokinetics of Nitroxide NMR Contrast Agents", Investigative Radiology, Nov.-Dec. 1984, vol. 19, pp. 53-562.
Brasch et al., "Work in Progess: Nuclear Magnetic Resonance Study of a Paramagnetic Nitroxide Contrast Agent for Enhancement of Renal Structures in Experimental Animals", Radiology, 147:773-779, Jun., 1983.
Butterfield, D. Allan, "Spin Labeling in Disease" in Biological Magnetic Resonance, L. J. Berliner et al., eds., vol. 4, 1982 Plenum Press, pp. 1-78.
Brasch et al., "Brain Nuclear Magnetic Resonance Imaging Enhanced by a Paramagnetic Nitroxide Contrast Agent: Preliminary Report" AJR 141, Nov. 1983, pp. 1019-1023.

Primary Examiner—Glennon H. Hollrah
Assistant Examiner—Gary E. Hollinden
Attorney, Agent, or Firm—Millen, White & Zelano

[57] ABSTRACT

Nitroxides useful as NMR contrast enhancing agents for organs are of the formula

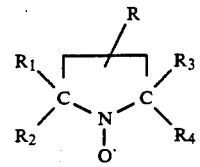

wherein in the above formulae, $R_1$, $R_2$, $R_3$ and $R_4$ are, g., $CH_3$; R is $-B-COO-M^+$ or $-B-N(alkyl)_3Hal^-$, wherein B is a divalent bond or alkylene of 1-8 carbon atoms, M is an ammonium or metal ion and Hal is a halogen atom; are also useful as NMR contrast enhancing agents on joints.

27 Claims, No Drawings

NITROXIDE NMR CONTRAST ENHANCING AGENTS AND THEIR USE IN NMR IMAGING

This is a continuation-in-part of Ser. No. 121,823 now abandoned, filed Nov. 6, 1987, as a continuation-in-part of Ser. No. 836,867, filed Mar. 7, 1986, now U.S. Pat. No. 4,834,964.

BACKGROUND OF THE INVENTION

This invention relates to NMR contrast (MRI) enhancing agents, especially for blood containing portion of the body and in joints, and to their use as such.

The use of NMR imaging as a diagnostic tool is less than 2 decades old. For a discussion of the history of the development of this technology, see Science 83, (1983), July/August Issue, pp. 60-65. For a general explanation of the technology, see Pykett, Ian L., Scientific American, 1982, May, pp. 81-88.

Medically useful NMR images presently are generated from the resonance of hydrogen nuclei provided by water and small, hydrogen-rich molecules in the body fluids and tissues. Differences in concentration, amounts, and source of these hydrogen nuclei in different regions of the body area being examined permits the generation by computer of images of that area. Proposed and established uses of NMR images include detection of tumors and other abnormalities of the brain, breast, kidney and lung, cancers, distinguishing benign from malignant tumors, detection of necrotic tissue and ischemia, diagnosing heart attacks, heart disease, degenerative diseases, strokes, arthritis and a variety of lesions, e.g., of the kidney and other organs, and evaluation of the effect of treatment on known cancerous tumors.

Notwithstanding the great potential of NMR in conjunction with a contrast enhancing agent as a soft tissue imaging technique, there are a variety of situations where current NMR technology generates a less than optimum image. One example is on joints, especially the knee joint. Therefore, there is considerable interest in NMR contrast-enhancing agents which, when present in the area around the joint, enhance the emitted signal by reducing the relaxation time of the blood or joint fluid in the area subjected to the NMR imaging.

NMR imaging agents are, by definition, paramagnetic, i.e., they have an unpaired electron. Polyvalent paramagnetic metal-containing compounds, e.g., organogadolinium compounds, are obvious candidates as NMR contrast enhancing agents but most are too toxic or irritating or present residual heavy metal deposition problems to be viable commercial products for in vivo use in human soft abdominal tissues or joints.

Nitroxides similarly have the theoretical potential for use commercially as in vivo NMR contrast enhancing agents because they meet several of the criteria required for all such products, e.g., prolonged storage stability at varying pH and temperature, feasible methods of preparation, good shelf life, chemical flexibility which permits structural variation to adapt to specific end-use environments, and longer spin relaxation times compared to inorganic paramagnetic ions. However, nitroxides generally are not practical for such use because they are rapidly enzymatically reduced in tissues to products which do not enhance the NMR signal. See "Pharmacokinetics of Nitroxide NMR Contrast Agents," Griffeth, et al., Invest. Radiol. 19:553-562 (1984), of which I am coauthor. Brasch, et al., in Radiology 147:773-779 (1983), report the successful enhancement of an NMR image with "TES", a piperidine mononitroxide stable free radical. Although that compound is stated by the authors to have an in vivo half life of 38 minutes, the dosage employed by them to achieve a substantial increase in intensity of signal from the renal parenchyma was huge, viz., 0.5 g/kg body weight by intravenous injection. Such a high dose suggests that the authors compensated for the rapid enzymatic reduction of the nitroxide by the use of such a massive dose of the nitroxide that it overwhelmed reductases in the tissue under study. I have found that unless the enzyme system is overwhelmed in this manner, the in vivo reduction of virtually all nitroxides is virtually instantaneous. Needless to say, such a procedure is contraindicated for human use. Because of the relatively low electrochemical potential, viz., about 300 mV, which is characteristic of all nitroxides having an isolated nitroxide group, the rapid enzymatic reduction and, accordingly, their limited half-life at acceptably low blood levels, have rendered nitroxides as a class poor candidates as commercially useful medical NMR image enhancing agents.

U.S. Pat. No. 3,704,235 is concerned with the preparation of tropane nitroxides. These compounds are quite toxic because they are reduced by enzymes such as FAD-containing monooxygenase to give superoxide. They are also too unstable to have a useful half-life in vivo.

U.S. Pat. No. 3,716,335 relates to the use of nitroxides as sensors of certain electron transfer reactions and is not related to the use of nitroxides as NMR contrast enhancing agents.

U.S. Pat. No. 3,702,831 relates to the use of nitroxides as magnetometer to monitor magnetic fields. This is only remotely related in that the magnetic field set-up by the free radical interacts with an applied field. Thus, the nitroxide becomes a marker, a probe. The compound used, viz., di-tert-butylnitroxide is rapidly eliminated in vivo.

U.S. Pat. No. 4,099,918 describes the synthesis of pyrrolidinoxyl as probes to study biological systems. There is no mention in this patent of NMR enhancing activity. Nitroxides have been used for years as probes of membrane structure.

Published European Patent Appln. 84 10 8900.6 discloses as stable NMR image enhancing agents nitroxides of the formula

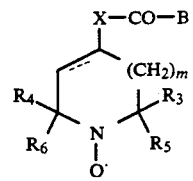

wherein B is a protein, sugar or lipid residue or $-NR_1R_2$.

Chem. Abstr. 88:134654s discloses 2,2,5,5-tetramethylpyrrolinyl-1-oxyl-saccharides.

Chem. Abstr. 90:137610b discloses a nitroxide of the formula

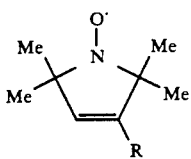

wherein R is —COOH or —CONH—C(CH₃)₂—OH.

French Application No. 73 23978 (Publication No. 2,235,103) discloses nitroxides of the formula

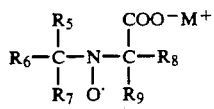

wherein R₁, R₂, R₃ and R₄ are alkyl.

Golding, B. T. et al, Synthesis, 1975, No. 7, 462–433, discloses nitroxides of the formulae

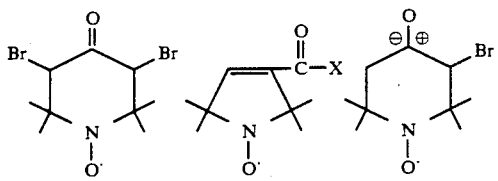

wherein X is OH, Cl, OC₂H₅, piperidino, anilino, benzylamino, hydroxyethylamino or carbethoxymethylamino.

I have found that although in general nitroxides have too short a half-life in blood to be useful as vascular NMR contrast enhancing agents, surprisingly within these classifiable are classes of nitroxides which are useful as vascular NMR contrast enhancing agents, as well as contrast enhancing agents for joints such as the knee.

OBJECTS OF THE INVENTION

It is an object of this invention to provide a method for producing an enhanced NMR image of a blood-containing portion of the body of a vertebrate. Another object is the provision of novel NMR contrast enhancing agents, especially for soft abdomen tissues (e.g., kidneys, spleen) and joints (e.g., knee). Other objects will be apparent to those skilled in the art to which this invention pertains.

SUMMARY OF THE INVENTION

In one method aspect, this invention relates to a method of enhancing the image obtained by NMR scanning of a joint, e.g., knee, elbow, hip or shoulder, which comprises injecting into the joint, prior to the NMR scan thereof in admixture with a non-toxic injectable pharmacologically acceptable aqueous vehicle, an amount of a charged, stable organic nitroxide of Formula (I) or (II) below, which is neurologically acceptable and non-toxic in the amount injected, effective to reduce the relaxation time of the fluids in the joint during the scanning period sufficiently to enhance the NMR image produced by the NMR scanning of the joint.

In another method aspect, this invention relates to a method of enhancing the image obtained by NMR scanning of the heart, kidney, liver, bladder or other organ receiving blood directly from the cardiovascular system, which comprises injecting into the vertebrate's blood stream, prior to the NMR scan of that organ, in admixture with a non-toxic injectable pharmacologically acceptable aqueous vehicle, an amount of a charged, stable organic nitroxide of Formula (I) which is neurologically acceptable and non-toxic in the amount injected, effective to reduce the relaxation time of the liquid in that organ during the scanning period sufficiently to enhance the NMR image produced by the scanning the organ.

In a composition aspect, this invention relates to compositions adapted for injection into joints or the blood comprising, in admixture with a pharmaceutically acceptable aqueous carrier, an NMR imaging enhancing concentration of a charged, stable organic nitroxide of Formula (I).

In another composition aspect, this invention relates to novel nitroxides.

DETAILED DISCUSSION

The term "charged" nitroxide as used herein means the nitroxide compound possesses, in addition to the nitroxyl group, a functional group which at physiological pH possesses a charge, either positive or negative, e.g., a carboxylic acid group or a quaternary ammonium group. Preferably, the nitroxide is fully charged, i.e., it is not in equilibrium with a non-charged species. Thus, quaternary ammonium nitroxides are preferred over carboxylic acids which, in turn, are preferred over primary, secondary and tertiary amines. Of the acidic nitroxides in equilibrium with a non-changed species, preferred are those having a pKa of less than 7.4, more preferably less than 5. Of the basic nitroxides, those with pKa greater than 7.4 are preferred.

The term "stable" as used herein means the nitroxide molecule totally and the nitroxyl moiety especially has an acceptable half-life when stored under ambient conditions, e.g., greater than 2 years and preferably greater than 5 years and when in aqueous solution is stable at room temperature for at least 2 hours and preferably at least 8 hours.

The term "neurologically acceptable" means that the nitroxide produces no short or long term adverse neurological effects. The term "non-toxic" means that no local or systemic toxic effects are manifested in the host by the nitroxide at the dosages required to achieve NMR image enhancement.

The charged nitroxides which can be employed in a method of this invention have certain structural features in common. As is well known, to be a stable free radical, both carbon atoms alpha to the nitroxyl group ordinarily must be fully substituted, i.e., they bear no hydrogen atoms, except a single hydrogen atom may be present if it is prevented from interacting with the nitroxyl group, e.g., by being acidic enough to be replaceable by a sodium ion. The simplest such substituents are alkyl, preferably of 1-8 carbon atoms, e.g., CH₃, C₂H₅, propyl, 2-propyl, butyl, 2-butyl, heptyl, octyl, etc., groups although other groups, such as alkyl groups substituted by one or more of hydroxy, halo, acyloxy, or a carbocyclic or heterocyclic aryl group, e.g., phenyl or pyridyl, may be present instead. Another requirement is that the nitroxide be water soluble. Ordinarily, the group imparting the requisite charge to the nitroxide compound, e.g., a carbocyclic, sulfonic or phosphonic acid or quaternary ammonium group will impart the requisite solubility thereto. However, other solubilizing groups may also be present in the molecule, if desired.

The preferred charged nitroxides employed in the method of this invention are very water soluble, e.g., at least one umole/ml., and preferably also have a low molecular weight, e.g., less than about 350, not including any associated metal or halogen ion, and are heterocyclic, preferably with only the nitroxide nitrogen atom as a hetero ring atom.

As stated above, physiologically the nitroxides employed in this invention are both neurologically and physiologically non-toxic and preferably are pharmacologically substantially inactive, at least at the minimum concentration required to achieve the desired image enhancement, and those of Formula I are resistant to rapid biodegradation by normal body mechanisms when injected into the blood stream. They are free of heavy metals, thereby avoiding the potential of residual mutagenic effects.

A class of charged nitroxides which meet the foregoing criteria are heterocyclic nitroxyl compounds of the formula

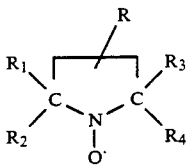

(I)

wherein
$R_1$, $R_2$, $R_3$ and $R_4$ each are alkyl or hydroxyalkyl of 1–4 carbon atoms, e.g., hydroxyethyl, 2-hydroxypropyl and 3-hydroxypropyl; and $R_2$ and/or $R_3$ additionally can be -alk-R', wherein alk is alkylene of 1–8, preferably 1–4, carbon atoms and R' is R, $-NH_2$, $-NHR_1$, or $-NR_1R_2$, wherein $R_1$ and $R_2$ are as defined above; and R is $-B-COO^-M^+$ or $-B-N^+(Alk)_3Hal^-$, wherein B is a divalent bond or alkylene of 1–8, preferably 1–4 carbon atoms and $M^+$ is an ammonium or metal ion, e.g., $NH_4^{++}$, $Na^+$ or $K^+$, and wherein Alk is alkyl of 1–8 carbon atoms or a corresponding alkyl group substituted by a free or esterified, e.g., by a lower fatty acid, preferably acetic acid, hydroxy group and $Hal^-$ is $Cl^-$, $Br^-$ or $I^-$.

Especially preferred among such compounds are those wherein $R_1$, $R_2$, $R_3$ and $R_4$ each are $CH_3$ or $C_2H_5$; those wherein $R_1$, $R_2$, $R_3$ and $R_4$ each are $CH_3$ and R is $-B-COO^-M^+$ wherein B is alkylene of 2 to 4 carbon atoms and $M^+$ is $Na^+$ or $K^+$; those wherein each of $R_1$, $R_2$, $R_3$ and $R_4$ is $CH_3$ or $C_2H_5$; and those wherein R is tri-lower-alkyl-ammonium halide in which each alkyl group is $CH_3$ or $C_2H_5$ and halide is chloride, bromide or iodide.

In addition to the nitroxides of Formula I, other examples of NMR image enhancing agents suitable for enhancement of the imaging of on joints (although not necessarily of the organs for which the compounds of Formula I are suitable) are water soluble compounds of the formula

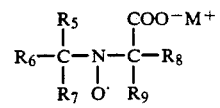

(II)

wherein $R_5$, $R_6$ and $R_7$ are the same or different and are alkyl, cycloalkyl, heterocyclic aliphatic, carbocyclic aryl or heterocyclic aryl, and preferably also are of up to 8 carbon atoms, e.g., each are methyl, ethyl, propyl, or butyl; $R_8$ and $R_9$ each are carbocyclic or heterocyclic aryl, e.g., phenyl, and $R_9$ additionally can be hydrogen, $R_8$ and $R_9$ collectively with the alpha carbon atom forms a cyclic group, for example, a cycloalkyl group, e.g., cyclopentyl or cyclohexyl and $M^+$ is as defined above. A specific example of a compound of Formula II is α-(N-t-butyl-nitroxyl)-phenylacetic acid, which is prepared by reacting 2 moles of lithio-diisopropylamine (LDA) with one mole of phenylacetic acid at $-70°$ C. in dry THF followed by one mole of 2-methyl-2-nitrosopropane. The thus-produced hydroxylamine is oxidized with a stream of air to produce the lithium salt of the desired nitroxide, which can be converted to other salts thereof in a conventional manner by passing through a cation exchange column. Examples of compounds of Formula I are water soluble salts of 2,5-dimethyl-2,5-bis(3-aminopropyl)-pyrrolidinyl-1-oxy and 2,5-dimethyl-2,5-bis(3-carboxypropyl)-pyrrolidinyl-1-oxy [Keana, J. F. W., et al., *J. Org. Chem.* 48:2644 (1983) and 51:4300 (1986).], e.g., the dioxalate and disodium salts, respectively and 2,2,5,5-tetramethyl-3-carboxy-pyrrolidinyl-1-oxy [Rozantzev, E. G., et al., Tetrahedron 21:491 (1965)], These compounds and others of Formulae I and II are useful as vascular NMR image enhancing agents.

Contemplated equivalents of the compounds of the invention are nitroxides bearing an additional substituent on a ring carbon atom thereof, e.g., alkyl, alkoxy, carboxy, carbalkoxy, halogen, nitro, etc., or instead of a group present thereon, a simple derivative thereof, e.g., an esterified hydroxy or carboxy group, an etherified hydroxy group, a halogenated or oxygenated alkyl group, provided water solubility and charge are not adversely affected.

The nitroxides of formulae I and II of this invention are useful for enhancing the NMR imaging on joints. The most common use of this type of contrast agent is assisting in the diagnosis of the extent of degeneration of or damage to a joint and/or the extent of recovery therefrom during chemo- or physiotherapy. Although NMR imaging without the aid of an imaging enhancing agent is capable of imaging a joint, the use of a contrast agent of this invention allows one to gain useful information while employing $T_1$-weighted imaging with its inherent high signal-to-noise ratio, thus making NMR a much more valuable diagnostic modality in the evaluation of this pathology. Although instillation of a contrast agent of this invention still involves injection into the joint, because the dose thereof is very low and the morbidity of the examination is close to zero, which is presently not the case with dye injections for X-ray examination.

The nitroxyl compounds of this invention are useful as NMR contrast enhancing agents for all vertebrates, i.e., in addition to human beings, other mammals and non-mammals.

The nitroxyl compounds of Formula I and most preferably 2,5-dimethyl-2,5-bis(3-aminoalkyl)-pyrrolidinyl-1-oxy and 2,5-dimethyl-2,5-bis(3-carboxyalkyl)-pyrrolidinyl-1-oxy wherein alkyl is 1–8 atoms, e.g., alkyl of the formula $-(CH_2)_n-$ wherein n is an integer from 0–8, preferably 2–4, when administered intravenously, can be employed as cardiovascular NMR imaging agents since they are "bioreductive resistant" paramagnetic species. They all can be used to enhance the NMR image on joints. For example, they can be used for the following purposes:

(a) Evaluating brain tumors and infarction, the latter being quite important because diffusion across the blood-brain barrier is dependent upon the structure of the nitroxide and the breakage of the barrier. For example, if there is a breakage due to an infarction, a charged, bioreductive-resistant nitroxide can enter the brain where otherwise the barrier prevents such diffusion.

(b) As contrast enhancement agents of body/abdominal NMR imaging. For example, depending upon charge, a number of these agents are taken up by the kidney and excreted. The high concentration of the nitroxides (noted, below) in the urine attests to the rapid elimination by the kidney, and permits NMR imaging of the bladder. These agents are useful for detection and differentiation of renal mass lesions, separation of adjacent structures, and assessment of the ureters and bladder, in a manner presently used for CAT scan and iodinated contrast agents. Similarly, such nitroxides are useful for contrast enhancement of other abdominal or retroperitoneal tissues.

(c) When bound to (or in) a colloidal or liposomal vehicle they are taken up by the reticuloendothelial system (RES) and thus are useful for detection of mass lesions or other pathological processes in the liver and spleen.

(d) Depending on structure they can be used to monitor pathologic states, e.g., hepatobiliary obstruction, renal ischemia/infarction, ureteral obstruction, as well as other tumors.

(e) As contrast enhancing agents for joints. For example, to determine the amount of inflammation in a knee.

The nitroxyl compound preferably is administered by injection as a single dose but can be administered in multiple doses or by continuous drip, e.g., in situations where NMR scans over several hours are contemplated. The amount administered is preferably that which achieves greater than 5%, preferably at least a 10% and more preferably at least 20% reduction in the $T_1$ relaxation time of the fluid in the area being scanned. Desirably in humans an initial dose of at least about 0.04 mmole is employed, e.g., from about 0.05 to 2 mmoles. Generally, individual doses of about 2–100 mg, preferably about 5–50 mg, are employed, depending on whether a joint or an organ is to be imaged.

For a description of the use of a nitroxide as an NMR image enhancing agent for renal structures, see Brasch, R. C. et al. Radiology 1983, 147: 773–779. When the heart or a portion of the cardiovascular system of a human being is to be imaged, the intravenous dosage of the nitroxyl compound generally will be about 1 to 5 g., e.g., about 1 to 10 mmol/kg.

The nitroxyl compound is ordinarily injected as a solution in a non-toxic injectable pharmacologically acceptable sterile aqueous vehicle, e.g., distilled water, physiological saline solution, or fluid withdrawn from the joint to be NMR scanned, or a mixture of either of the latter two and either of the former two. The aqueous vehicle can also contain other ingredients conventionally present in diagnostic fluids injected into the spine or blood, e.g., NaCl, buffer, etc.

In a composition aspect, this invention relates to pharmaceutical compositions adapted for injection into either the blood or joint comprising a charged nitroxide of this invention, e.g., those comprising an amount of a sterile solution of a concentration of about 1 to 50 mM, preferably about 10 mM, in an aqueous vehicle, of a charged organic nitroxide which is neurologically and physiologically non-toxic and effective to reduce the relaxation time of the area under study during the scanning period sufficiently to enhance the NMR image produced by the scanning. For example, the nitroxide or a solution thereof can be contained in sterile form in a conventional sealed ampoule or vial, in single or multiple dosage form, and can be at the desired injection concentration or it can be in a more concentrated form so that it can be mixed with the aqueous vehicle prior to injection.

In another composition aspect, this invention relates to pharmaceutical compositions adapted for intravenous injection comprising a sterile solution in an aqueous vehicle at a concentration effective to reduce the relaxation time of at least one of blood and urine during the NMR scanning period sufficiently to enhance the NMR image produced by the NMR scanning of the blood or urine of a mammal intravenously injected with the composition, of a compound of one of Formulae I and II.

In another method of use aspect this invention relates to a method of enhancing the image obtained by NMR scanning of the blood, urine or an organ associated with the cardiovascular system of an animal, which comprises injecting into the blood of the animal, prior to the NMR scan of the portion of the body to be imaged, in admixture with a non-toxic injectable pharmacologically acceptable aqueous vehicle, an amount effective during the scanning period to reduce the relaxation time of the fluid in the portion of the body being scanned, to enhance the NMR image produced by the scanning, of a charged, stable organic nitroxide which is neurologically acceptable and non-toxic in the amount injected of a compound of one of Formulae I and II.

Since the molar concentration of stable nitroxides generally required to achieve sufficient relaxation time of a body fluid to enhance an NMR image of, e.g., blood, urine or an organ receiving blood directly from the cardiovascular system, e.g., brain, heart, kidney, liver, etc., can be calculated theoretically, the amount of a nitroxide of this invention which must be administered intravenously to achieve, after dilution by the blood of the mammal, image enhancement of the organ or fluid, can readily be determined by precalculation and routine experimentation.

Alternatively, the nitroxide can be stored in dry form in a conventional sealed vial, either alone or in admixture with a conventional solution-promoting water-soluble compound and formed into the desired injectable solution just prior to injection.

Conventional NMR scanning procedures can be employed in the method of this invention, e.g., those described by DiChino, G., et al., Radiology 1985, 157:373-7; and Portugal, F. H., High Technology 1984, Aug. 66–73.

Without further elaboration, it is believed that one skilled in the art can, using the preceding description, utilize the present invention to the fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLES

Preparation 4

(N,N,N-dimethylethylamino)-2,2,6,6-tetramethyl-piperidinoxyl Iodide 2,2,6,6-tetramethyl-4-piperidone (I)

This compound was prepared according to the method of Sandris and Ourisson, Bull. Soc. Chim. Fr. 25: 345 (1958), in which 25 gms (180 mmoles) of phorone and 180 mls of ammonium hydroxide are stirred at 35° C. for 12 hrs. The solution is then cooled in an ice bath and concentrated HCl is added until the pH of the solution is 1. This solution is then saturated with NaCl and extracted with ether. The pH of the remaining liquid is raised to 10 with ammonium hydroxide followed by ether extraction. The ether solution is then dried with anhydrous sodium sulfate and evaporated to dryness, in vacuo, giving 20 gms (78%) of the desired product, B. P. 80°-85° C. at 15 mm Hg.

4-oxo-2,2,6,6 tetramethylpiperidinoxyl (II)

To a solution containing 7.5 g (48.8 mmoles) of 2,2,6,6-tetramethyl-4-piperidone, 0.75 gms of sodium tungstate, and 0.75 gms of EDTA in 50 ml of water was added 10 ml of 30% hydrogen peroxide. The mixture was stirred at room temperature for 48 hrs, filtered, saturated with NaCl and the pH lowered to 3-4. This solution was extracted with ether giving a red oil. Chromatographic separation using neutral alumina and methylene chloride gave 6.9 g (84%) of a red solid, M.P. 33°-35° C., E. G. Rozantsev, "Free Nitroxyl Radicals", Plenum Press, New York, pp. 213-214 (1970).

4-(N,N-dimethylethylamino)-2,2,6,6-tetramethyl-piperidinoxyl iodide (IV)

To a solution of 28.7 gms (352 mmoles) of dimethylamine:HCl dissolved in 150 ml of methanol at pH 7-8 was added 1 gm (58.8 mmoles) of (II) and 0.22 gms (35.2 mmoles) of NaBH$_3$CN and 3A molecular sieves. The reaction was stirred at room temperature for 24 hrs, filtered and the solution was evaporated to dryness in vacuo. The remaining oil was taken up in water, saturated with NaCl, the pH lowered to 3-4, and then extracted with ether. The remaining water solution was made basic with 10% NaOH and extracted with ether, and dried over anhydrous MgSO$_4$. This solution was evaporated to dryness giving a red oil (III). The infrared spectrum of this oil no longer contained a carbonyl peak. The oil was then dissolved in ether to which excess ethyl iodide was added. Soon after the addition, a precipitate formed which was filtered and recrystallized from 95% ethanol giving (IV), M.P. 208°-210° C.

EXAMPLE 1

Stability of Nitroxide in CSF

Dogs (data is the average of 4 independent studies) under general anesthetic were injected with 2 ml of a 10 mM stock solution of 4-(N,N,N-dimethylethylamino)-2,2,6,6-tetramethylpiperidin-oxyl iodide in saline (0.90%) into the spinal cavity (3 cm below the head). At defined times, samples of CSF were removed from a catheter inserted at the point of injection. The samples were analyzed for nitroxide concentration and relaxation times. (A separate experiment determined that charged nitroxides are not bioreduced by CSF fluid. Therefore, the diminution in nitroxide concentration is attributed to active transport from the spinal cavity.) The data obtained are set forth in the table below.

EXAMPLE 2

Follow the procedure of Example 1, employing as the charged nitroxide 0.04 millimoles of 4-(N,N-dimethyl-N-2'-hydroxyethylamino)-2,2,6,6-tetramethyl-piperidinoxyl chloride. (Kornberg and McConnell, Biochemistry, Vol. 10, No. 7, 1971, pp. 1111-1120.)

EXAMPLE 3

Follow the procedure of Example 1, employing as the charged nitroxide 0.04 millimoles of a spin labeled analog of acetylcholine, namely 2-(N,N-dimethyl-N-(2,2,6,6-tetramethylpiperidinoxylamino) ethyl acetate iodide or 4-trimethylaminomethyl-4-acetoxy-2,2,6,6-tetramethylpiperidinoxyl iodide. Rosen, G. M., Abou-Donia, M. B., Synthetic Communication 1975;5:415-422; Rauckman, E. J., Rosen, G. M., Abou-Donia, M. B., J. Org. Chem. 1976; 41:564; ibid, Org. Pre. Pro. Int. 1976;8:159-161.

EXAMPLE 4

Follow the procedure of Example 1, employing as the charged nitroxide 0.04 millimoles of the sodium salt of 1-oxyl-2,2,5,5-tetramethyl-3-pyrroline-3-carboxylic acid. (Hankovszky, H. O., Acta. Chim. Acad. Sci. Hung. 1978, 98(3), 339-48; C.A. 90:17,23 April (1979, p. 494) Vol. 37610b.

EXAMPLE 5

A. 0.5 mmol/kg of a sterile one molar solution in distilled water of the sodium salt of 3-carboxy-2,2,5,5-tetramethyl pyrrolidinyl-1-oxyl was injected intravenously into a rat. After 15 minutes, the animal was sacrificed and aliquots of blood and urine (removed by a hypodermic needle from the heart and bladder) of the rat and various tissues (surgically removed, pat-dried with a paper towel and homogenized) were analyzed for nitroxide concentration.

B. The above procedure was followed with 0.5 mmol/kg of 2,5 dimethyl-2.5-bis-(3-aminopropyl)pyrrolidinyloxyl.

C. The above procedure was followed with 0.2 mmol/kg of the sodium salt of (N-t-butylnitroxyl)-p-(trimethylamino) phenylacetic acid iodide.

The resultant 15-minute post-injection nitroxide concentrations are set forth in the table below.

| TISSUE | NITROXIDE CONCENTRATION COMPOUND | | |
|---|---|---|---|
| | 7A | 7B | 7C |
| Liver (n mol/g) | 24.6 | 2,360 | 89 |
| Kidney (n mol/g) | 461 | 11,400* | 4,800* |
| Lung (n mol/g) | .122 | 1040 | 865 |
| Heart (n mol/g) | 95.8 | 707 | 236 |
| Brain (n mol/g) | 17.6 | 176 | 302 |
| Blood (mM) | 0.36* | 1.4* | 1.34* |
| Urine (mM) | 7.8* | 5.5* | 16.6* |

*Nitroxide concentration was high enough to alter the $T_1$.

It is apparent from the nitroxide concentrations in the urine that the three nitroxides are rapidly concentrated therein.

EXAMPLE 6

Follow the procedure of Example 5A employing as the nitroxide the sodium salt of 2,2,5,5-tetramethyl-3-(1'-carboxy-propyl-2')-pyrrolidyloxy, which can be produced as follows: add 1 mol. equiv. of n-butyllithium in hexane slowly with stirring at 0° C. to diisopropylamide under $N_2$. Cool to −78° C. and then add thereto 1 mol. e.g. of t-butyltrimethylsilyl acetate. Stir for 20 min. at that temperature and then add thereto 1 mol. equiv. of 2,2,5,5-tetramethyl-3-acetyl-pyrrolidinyl-1-oxy to produce 2,2,5,5-tetramethyl-3-[1'-methyl-2'-(carbo-t-butoxy)-vinyl-pyrrolidinyl-1-oxy. Allow the temperature to rise to −2° C., stir for one hour, allow to warm to 0° and then add thereto a concentrated solution of $NH_4Cl$. Isolate the product and simultaneously hydrogenate the double bond and reduce to nitroxide group to an amine with $H_2$ and Raney nickel, followed by reoxidation of the latter with $H_2O_2$, using sodium tungstate as oxidation catalyst. Hydrolyze the ester group with a 10% molar excess of NaOH to give the sodium salt of the desired product. Neutralize the solution with HCl and extract the desired product with ether.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of enhancing the image obtained by NMR scanning of an organ associated with the cardiovascular system of a human being which comprises injecting into the blood of the human being, prior to the NMR scan on the organ, in admixture with a non-toxic injectable pharmacologically acceptable aqueous vehicle, an amount which is both nontoxic and effective to reduce the relaxation time of the blood during the scanning period sufficiently to enhance the NMR image produced by the scan of a charged, stable organic nitroxide of the formula:

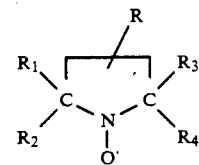

wherein
$R_1$, and $R_4$ each are alkyl or hydroxyalkyl of 1–4 carbon atoms;
$R_2$ and $R_3$ each are alkyl, hydroxyalkyl of 1–4 carbons or —alk—R', in which alk is alkylene of 1–8 carbon atoms and R' is R as defined below, —$NH_2$, —$NHR_1$, or —$NR_1R_2$, in which $R_1$ and $R_2$ are alkyl or hydroxyalkyl of 1–4 carbon atoms; and
R is —alk—$COO^-M^+$ or —B—$N^+(Alk)_3Hal^-$ in which alk is as defined above, B is a divalent bond or alk as defined above and $M^+$ is an ammonium or metal ion, Alk is alkyl of 1–8 carbon atoms or a corresponding alkyl group substituted by a free or esterified hydroxy group, and $Hal^-$ is $Cl^-$, $Br^-$ or $I^-$.

2. A method according to claim 1, wherein R is —B—$N^+(Alk)_3Hal^-$ as defined therein.

3. A method according to claim 2, wherein $R_1$, $R_2$, $R_3$ and $R_4$ each are $CH_3$ wherein B is alkylene of 1–4 carbon atoms and wherein Alk is alkyl of 1 to 4 carbon atoms.

4. A method according to claim 2, wherein $R_1$, $R_2$, $R_3$ and $R_4$ each are $CH_3$, wherein B is a divalent bond and wherein Alk is alkyl of 1 to 4 carbon atoms.

5. A method according to claim 1, wherein the nitroxide is 3-(N,N,N-dimethylethylamino)-2,2,5,5-tetramethylpyrrolidin-1-oxyl iodide.

6. A method according to claim 1, wherein R is —alk—$COO^-M^+$ as defined therein.

7. A method according to claim 6, wherein $R^1$, $R^2$, $R^3$ and $R_4$ each are $CH_3$.

8. A method according to claim 6, wherein $R_1$, $R_2$, $R_3$ and $R_4$ each are $CH_3$, and $M^+$ is $Na^+$ or $K^+$.

9. A method according to claim 1, wherein the nitroxide is the sodium salt of 2,2,5,5l-tetramethyl-3l-(1'-carboxy-propyl-2')pyrrolidyl-1-oxy.

10. A method of enhancing the image obtained by NMR scanning of the joint of an animal which comprises injecting into the joint of the animal, prior to the NMR scan on the joint, in admixture with a non-toxic injectable pharmacologically acceptable aqueous vehicle, an amount which is both non-toxic and effective to enhance the NMR image produced by the scan of a neurologically acceptable and nontoxic charged, stable organic nitroxide of the formula:

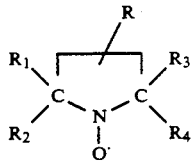

wherein
$R_1$, and $R_4$ each are alkyl or hydroxyalkyl of 1–4 carbon atoms;
$R_2$ and $R_3$ each are alkyl, hydroxyalkyl of 1–4 carbons or —alk—R', in which alk is alkylene of 1–8 carbon atoms and R' is R as defined below, —$NH_2$, —$NHR_1$, or —$NR_1R_2$, in which $R_1$ and $R_2$ each are alkyl or hydroxyalkyl of 1–4 carbon atoms; and
R is —alk—$COO^-M^+$ or —B—$N^+(Alk)_3Hal^-$ in which alk is as defined above, B is a divalent bond or alk as defined above and $M^+$ is an ammonium or metal ion, Alk is alkyl of 1–8 carbon atoms or a corresponding alkyl group substituted by a free or esterified hydroxy group, and $Hal^-$ is $Cl^-$, $Br^-$ or $I^-$.

11. A method according to claim 10, wherein R is —B—$N^+(Alk)_3Hal^-$ as defined therein.

12. A method according to claim 1, wherein $R_1$, $R_2$, $R_3$ and $R_4$ each are $CH_3$, wherein B is alkylene of 1 to 4 carbon atoms and Alk is alkyl of 1 to 4 carbon atoms.

13. A method according to claim 1, wherein $R_1$, $R_2$, $R_3$ and $R_4$ each are $CH_3$, wherein B is a divalent bond and wherein Alk is alkyl of 1 to 4 carbon atoms.

14. A method according to claim 10, wherein the nitroxide is 3-(N,N,N-dimethylethylamino)-2,2,5,5-tetramethylpyrrolidin-1-oxyl iodide.

15. A method according to claim 10, wherein R is —alk—COO$^-$M$^+$ as defined therein.

16. A method according to claim 15, wherein R$^1$, R$^2$, R$^3$ and R$_4$ each are CH$_3$.

17. A method according to claim 15, wherein R$_1$, R$_2$, R$_3$ and R$_4$ each are CH$_3$, and M$^+$ is Na$^+$ or K$^+$.

18. A method according to claim 10, wherein the nitroxide is the sodium salt of 2,2,5,5-tetramethyl-3-(1'-carboxy-propyl-2')pyrrolidyl-1-oxy.

19. A pharmaceutical composition adapted for injection into the blood intravenously or into the joint of a human being comprising per unit dosage amount a nontoxic NMR image enhancing amount in a sterile solution vehicle of a charged, stable organic nitroxide of the formula

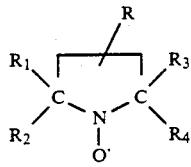

wherein

R$_1$, and R$_4$ each are alkyl or hydroxyalkyl of 1–4 carbon atoms;

R$_2$ and R$_3$ each are alkyl, hydroxyalkyl of 1–4 carbons or —alk—R', in which alk is alkylene of 1–8 carbon atoms and R' is R as defined below, —NH$_2$, —NHR$_1$, or —NR$_1$R$_2$, in which R$_1$ and R$_2$ each are alkyl or hydroxyalkyl of 1–4 carbon atoms; and R is —alk—COO$^-$M$^+$ or —B—N$^+$(Alk)$_3$Hal$^-$ in which alk is as defined above, B is a divalent bond or alk as defined above and M$^+$ is an ammonium or metal ion, Alk is alkyl of 1–8 carbon atoms or a corresponding alkyl group substituted by a free or esterified hydroxy group, and Hal$^-$ is Cl$^-$, Br$^-$ or I$^-$.

20. A composition according to claim 19, wherein R is —B—N$^+$(Alk)$_3$Hal$^-$ as defined therein.

21. A composition according to claim 20, wherein R$_1$, R$_2$, R$_3$ and R$_4$ each are CH$_3$ wherein B is alkylene of 1 to 4 carbon atoms and wherein Alk is alkyl of 1 to 4 carbon atoms.

22. A composition according to claim 19, wherein R$_1$, R$_2$, R$_3$ and R$_4$ each are CH$_3$, wherein B is a divalent bond, and wherein Alk is alkyl of 1 to 4 carbon atoms.

23. A composition according to claim 19, wherein the nitroxide is 3-(N,N,N-dimethylethylamino)-2,2,5,5-tetramethylpyrrolidin-1-oxyl iodide.

24. A composition according to claim 19, wherein R is —alk—COO$^-$M$^+$ as defined therein.

25. A composition according to claim 24, wherein R$^1$, R$^2$, R$^3$ and R$^4$ each are CH$_3$.

26. A composition according to claim 24, wherein R$_1$, R$_2$, R$_3$ and R$^4$ each are CH$_3$, wherein B is alkylene of 2–4 carbon atoms and M$^+$ is Na$^+$ or K$^+$.

27. A composition according to claim 19, wherein the nitroxide is the sodium salt of 2,2,5,5l-tetramethyl-3-(1'-carboxy-propyl-2')pyrrolidyl-1-oxy.

* * * * *